US012721505B2

(12) United States Patent
Kunuki et al.

(10) Patent No.: US 12,721,505 B2
(45) Date of Patent: Sep. 1, 2026

(54) BENDABLE PART OF ENDOSCOPE, ENDOSCOPE, AND MOVABLE MEMBER

(71) Applicant: FUJIFILM Corporation, Tokyo (JP)

(72) Inventors: Yoshiyuki Kunuki, Ashigarakami-gun (JP); Kimitake Fukushima, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 207 days.

(21) Appl. No.: 18/518,583

(22) Filed: Nov. 23, 2023

(65) Prior Publication Data

US 2024/0206715 A1 Jun. 27, 2024

(30) Foreign Application Priority Data

Dec. 27, 2022 (JP) ................................. 2022-209562

(51) Int. Cl.
*A61B 1/005* (2006.01)
*A61B 1/008* (2006.01)

(52) U.S. Cl.
CPC .......... *A61B 1/0055* (2013.01); *A61B 1/0057* (2013.01); *A61B 1/008* (2013.01)

(58) Field of Classification Search
CPC ..... A61B 1/0055; A61B 1/0057; A61B 1/008; A61B 1/005; A61B 2017/00314; A61B 2034/306
See application file for complete search history.

(56) References Cited

U.S. PATENT DOCUMENTS

| | | | |
|---|---|---|---|
| 2003/0083550 | A1 | 5/2003 | Miyagi |
| 2004/0199052 | A1 | 10/2004 | Banik et al. |
| 2005/0075538 | A1 | 4/2005 | Banik et al. |
| 2008/0269561 | A1 | 10/2008 | Banik et al. |

(Continued)

FOREIGN PATENT DOCUMENTS

| | | |
|---|---|---|
| EP | 3603900 | 7/2022 |
| JP | H0690894 | 4/1994 |

(Continued)

OTHER PUBLICATIONS

"Notice of Reasons for Refusal of Japan Counterpart Application", issued on Jun. 30, 2026, with English translation thereof, p. 1-p. 7.

*Primary Examiner* — Michael J Carey
*Assistant Examiner* — Dayton Hyun Jin Barker
(74) *Attorney, Agent, or Firm* — JCIPRNET

(57) ABSTRACT

A bendable part of an endoscope that is provided in an insertion part of the endoscope, includes: a plurality of movable members that are arranged in an axial direction of the insertion part, each of the movable members includes a body part having a tubular shape, a pair of first protruding portions, and a pair of second protruding portions as defined herein, one of the pair of first protruding portions is provided with a first recessed portion, other of the pair of first protruding portions is provided with a first projecting portion, one of the pair of second protruding portions is provided with a second recessed portion, other of the pair of second protruding portions is provided with a second projecting portion, and one of two adjacent ones of the movable members and other of the two adjacent ones of the movable members are as defined herein.

16 Claims, 16 Drawing Sheets

(56) References Cited

U.S. PATENT DOCUMENTS

| | | | | |
|---|---|---|---|---|
| 2010/0056868 | A1 * | 3/2010 | Kitagawa | G02B 23/2407 600/141 |
| 2012/0165608 | A1 | 6/2012 | Banik et al. | |
| 2014/0088358 | A1 | 3/2014 | Banik et al. | |
| 2014/0378767 | A1 | 12/2014 | Lee et al. | |
| 2016/0316996 | A1 * | 11/2016 | Nakayama | A61B 34/71 |
| 2018/0168432 | A1 | 6/2018 | Banik et al. | |
| 2019/0261830 | A1 | 8/2019 | Banik et al. | |
| 2020/0359874 | A1 | 11/2020 | Banik et al. | |
| 2021/0076905 | A1 | 3/2021 | Banik et al. | |
| 2022/0233055 | A1 | 7/2022 | Banik et al. | |

FOREIGN PATENT DOCUMENTS

| | | | | |
|---|---|---|---|---|
| JP | 2000023908 | | 1/2000 | |
| JP | 2003135381 | | 5/2003 | |
| JP | 2008295774 | | 12/2008 | |
| JP | 2010158566 | | 7/2010 | |
| JP | 2020515330 | | 5/2020 | |
| JP | 2022-209562 | * | 12/2022 | A61B 1/008 |
| WO | WO2017145467 A1 | * | 8/2017 | G02B 23/24 |

* cited by examiner 42
30G
30G
30G
30D(30)
30C(30)
30G
30B(30)
30A(30)
30G
41
1b
43
43
Y
X
Z 30(30B)
32U
320U
33Ua
33U
PL1
33R
33Ra
320R
32R
32Da
32D
320D
PD2
PD1
31D
31
31L
320L
PL2
32L
Y
Z
X E2
E3
31D
320D
E1
32Da
32D
31

BENDABLE PART OF ENDOSCOPE, ENDOSCOPE, AND MOVABLE MEMBER

CROSS-REFERENCE TO RELATED APPLICATIONS

The present application claims priority under 35 U.S.C. § 119 to Japanese Patent Application No. 2022-209562, filed on Dec. 27, 2022. The above application is hereby expressly incorporated by reference, in its entirety, into the present application.

BACKGROUND OF THE INVENTION

1. Field of the Invention

The present invention relates to a bendable part of an endoscope, an endoscope including the bendable part, and a movable member used in the bendable part.

2. Description of the Related Art

JP2008-295774A discloses an endoscope bendable part including a plurality of nodal rings each having a tubular portion and arranged coaxially with each other, in which one nodal ring of two adjacent nodal rings includes a protruding portion that is provided integrally with the tubular portion and that extends in a radial direction of the tubular portion, and the other nodal ring of the two adjacent nodal rings includes a receiving part that is provided integrally with the tubular portion and to which the protruding portion is inserted to be rotatable about a longitudinal axis of the protruding portion.

JP1994-090894A (JP-H06-090894A) discloses a bendable tube nodal ring for an endoscope, which is configured by rotatably connecting, via a rivet member, a plurality of nodal rings while their connecting portions overlap each other and which can be operated to bend via an operating part.

JP2003-135381A discloses a bendable tube comprising a plurality of articulated rings that are arranged in a row at intervals such that adjacent articulated rings do not overlap each other and a connecting mechanism that spans from one of the adjacent articulated rings to the other of the adjacent articulated rings, in which a hinge attachment portion is disposed on a peripheral surface of the articulated ring, the connecting mechanism includes a pair of hinge members that are rotatably connected around a rotation axis orthogonal to a direction of the arrangement, one hinge member is fixed to the hinge attachment portion of the one articulated ring by fixing means such as welding, brazing, or bonding, and the other hinge member is fixed to the hinge attachment portion of the other articulated ring by the same fixing means as above.

JP2000-23908A discloses a multi-joint bending mechanism in which a plurality of elements are connected to be alternately rotatable about axes orthogonal to each other and are bent by pulling a wire cable inserted into wire guides provided on inner peripheral sides of the elements.

JP2010-158566A discloses an imaging endoscope comprising a shaft including a proximal end, a distal end, and one or more holes therein, and one or more light emitting diodes provided on or adjacent to the distal end of the shaft for illuminating a tissue, an imaging assembly provided at the distal end of the shaft and including an image sensor that generates an image of the tissue, several control cables that are selectively pulled to bend the shaft in a desired direction, a deformable articulated joint including several links that are joined together by spring segments and bendable under pulling tension of one or more control cables, and a sheath on the articulated joint.

SUMMARY OF THE INVENTION

It is preferable, in terms of manufacturing, that a plurality of bending pieces constituting a bendable part of an endoscope can be easily connected to each other. The technologies disclosed in JP2008-295774A, JP1994-090894A (JP-H06-090894A), JP2003-135381A, JP2000-23908A, and JP2010-158566A have room for improvement regarding connection of the bending pieces.

An object of the present disclosure is to provide a bendable part of an endoscope that is easily manufactured and an endoscope including the bendable part.

A bendable part of an endoscope according to one aspect of the technology of the present disclosure is a bendable part provided in an insertion part of the endoscope, the bendable part comprising a plurality of movable members that are arranged in an axial direction of the insertion part, in which the movable member includes a body part having a tubular shape, a pair of first protruding portions that protrude to one side in the axial direction from the body part and that face each other across an axis of the body part, and a pair of second protruding portions that protrude to the other side in the axial direction from the body part and that face each other across the axis of the body part, one of the pair of first protruding portions is provided with a first recessed portion that extends in a radial direction of the body part, the other of the pair of first protruding portions is provided with a first projecting portion that extends in the radial direction, one of the pair of second protruding portions is provided with a second recessed portion that extends in the radial direction of the body part, the other of the pair of second protruding portions is provided with a second projecting portion that extends in the radial direction, and in a case where one of two adjacent movable members is a first movable member and the other is a second movable member, the first recessed portion of the first movable member engages with the second projecting portion of the second movable member, and the first projecting portion of the first movable member engages with the second recessed portion of the second movable member.

A movable member according to another aspect of the technology of the present disclosure is a movable member in a bendable part of an endoscope in which the bendable part is configured by connecting a plurality of the movable members arranged in an axial direction of an insertion part of the endoscope, the movable member comprising: a body part having a tubular shape; a pair of first protruding portions that protrude to one side in the axial direction from the body part and that face each other across an axis of the body part; and a pair of second protruding portions that protrude to the other side in the axial direction from the body part and that face each other across the axis of the body part, in which one of the pair of first protruding portions is provided with a first recessed portion that extends in a radial direction of the body part, the other of the pair of first protruding portions is provided with a first projecting portion that extends in the radial direction, one of the pair of second protruding portions is provided with a second recessed portion that extends in the radial direction of the body part, and the other of the pair of second protruding portions is provided with a second projecting portion that extends in the radial direction.

According to the present invention, it is possible to easily manufacture the bendable part of the endoscope.

BRIEF DESCRIPTION OF THE DRAWINGS

FIG. 13 is an exploded perspective view of the movable member group 30G shown in

FIG. 12.

FIG. 14 is a perspective view showing a configuration of a movable member 30X which is a modification example of the movable member 30.

DESCRIPTION OF THE PREFERRED EMBODIMENTS

Figure 1:
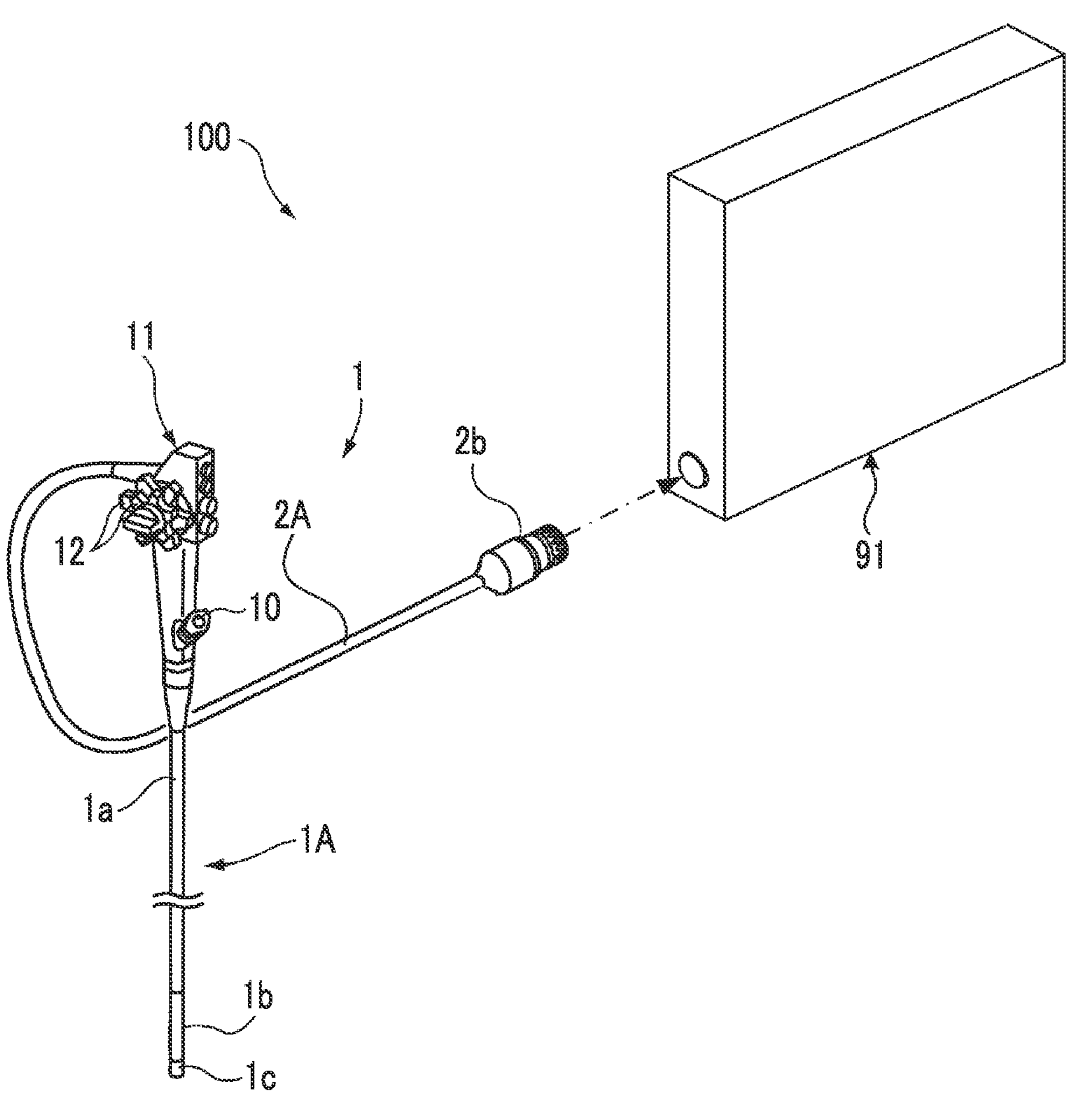
FIG. 1 is a schematic perspective view of an endoscope system 100 provided with an endoscope 1, which is an embodiment of the present invention.

FIG. 1 is a schematic perspective view of an endoscope system 100 comprising an endoscope 1, which is an embodiment of the present invention. The endoscope system 100 comprises the endoscope 1 and a case 91. The case 91 incorporates a tablet terminal and an interface adapter that connects the tablet terminal to the endoscope 1.

The endoscope 1 comprises an insertion part 1A that is a tubular member extending in one direction and that is inserted into a body cavity as an object to be observed, an operating device 11 that is provided to be continuous at a proximal end part of the insertion part 1A and that is provided with an operating member for performing a forceps operation, a suction operation, and the like, and a cable 2A, such as a universal cord, including a connector portion 2*b* that attachably and detachably connects the endoscope 1 to the interface adapter of the case 91. The insertion part 1A is formed of a flexible tube or the like. The endoscope 1 is for single use, but is not limited thereto. It should be noted that the single-use endoscope is not strongly required to have liquid tightness and durability.

The insertion part 1A is composed of a flexible soft portion 1*a*, a bendable part 1*b* provided at a distal end of the soft portion 1*a*, and a rigid distal end portion 1*c* provided at a distal end of the bendable part 1*b*. The bendable part 1*b* is configured to be bendable through a rotating operation of two angle knobs 12 provided on the operating device 11. The bendable part 1*b* can be bent in any direction and at any angle depending on a site of a subject or the like for which the endoscope 1 is used, and the distal end portion 1*c* can be directed in a desired direction.

In the following description, an axial direction of the insertion part 1A will be referred to as a direction Z, and two directions perpendicular to the direction Z and orthogonal to each other will be referred to as a direction X and a direction Y. Each of the direction X and the direction Y constitutes a radial direction of the insertion part 1A.

Figure 2:
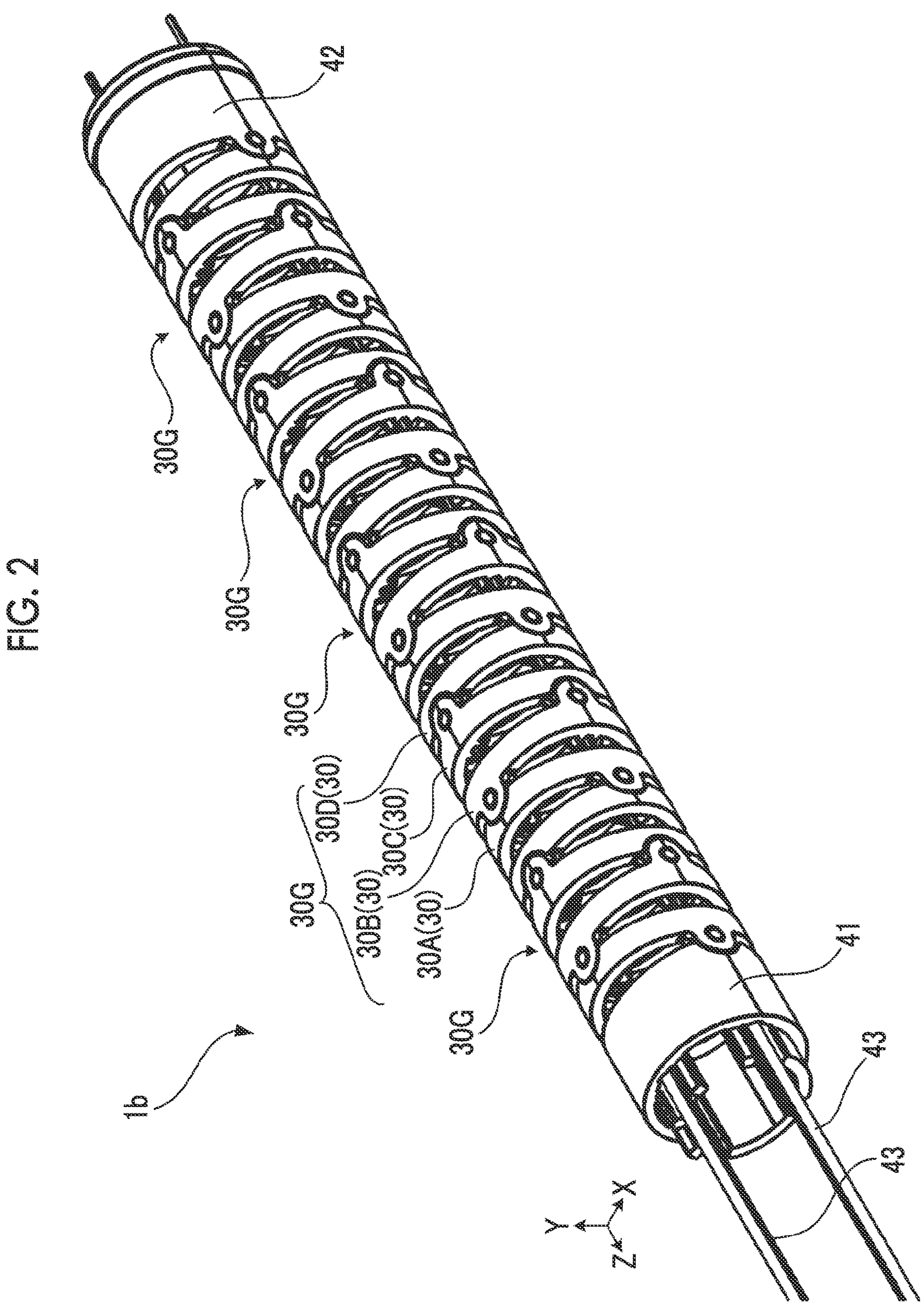
FIG. 2 is a perspective view schematically showing a main part of a bendable part 1*b* of the endoscope 1 shown in FIG. 1.

FIG. 2 is a perspective view schematically showing a main part of the bendable part 1*b* of the endoscope 1 shown in FIG. 1. The bendable part 1*b* comprises a plurality of movable members 30 that are arranged in the direction Z, a proximal end-side connecting member 41 that connects a most proximal end-side movable member among the plurality of movable members 30 to the soft portion 1*a*, a distal end-side connecting member 42 that connects a most distal end-side movable member among the plurality of movable members 30 to the distal end portion 1*c*, and a plurality of (four in the illustrated example, but only two are shown) wires 43 which are inserted into each of the movable members 30, the proximal end-side connecting member 41, and the distal end-side connecting member 42.

Each of the plurality of wires 43 passes through the soft portion 1*a* and is connected to a bending operating part 10 of the operating device 11. Each of the movable members 30, the proximal end-side connecting member 41, and the distal end-side connecting member 42 are made of a metal, a resin, or the like. In a case of a single-use endoscope, since the above-described members are made of a resin, manufacturing costs can be reduced. Each of the movable members 30, the proximal end-side connecting member 41, and the distal end-side connecting member 42 are covered with a covering member (not shown).

The plurality of movable members 30 include five movable member groups 30G each consisting of a movable member 30A, a movable member 30B connected to the movable member 30A, a movable member 30C connected to the movable member 30B, and a movable member 30D connected to the movable member 30C, and have a configuration in which the five movable member groups 30G are connected. The plurality of movable members 30 have the same shape.

Figure 3:
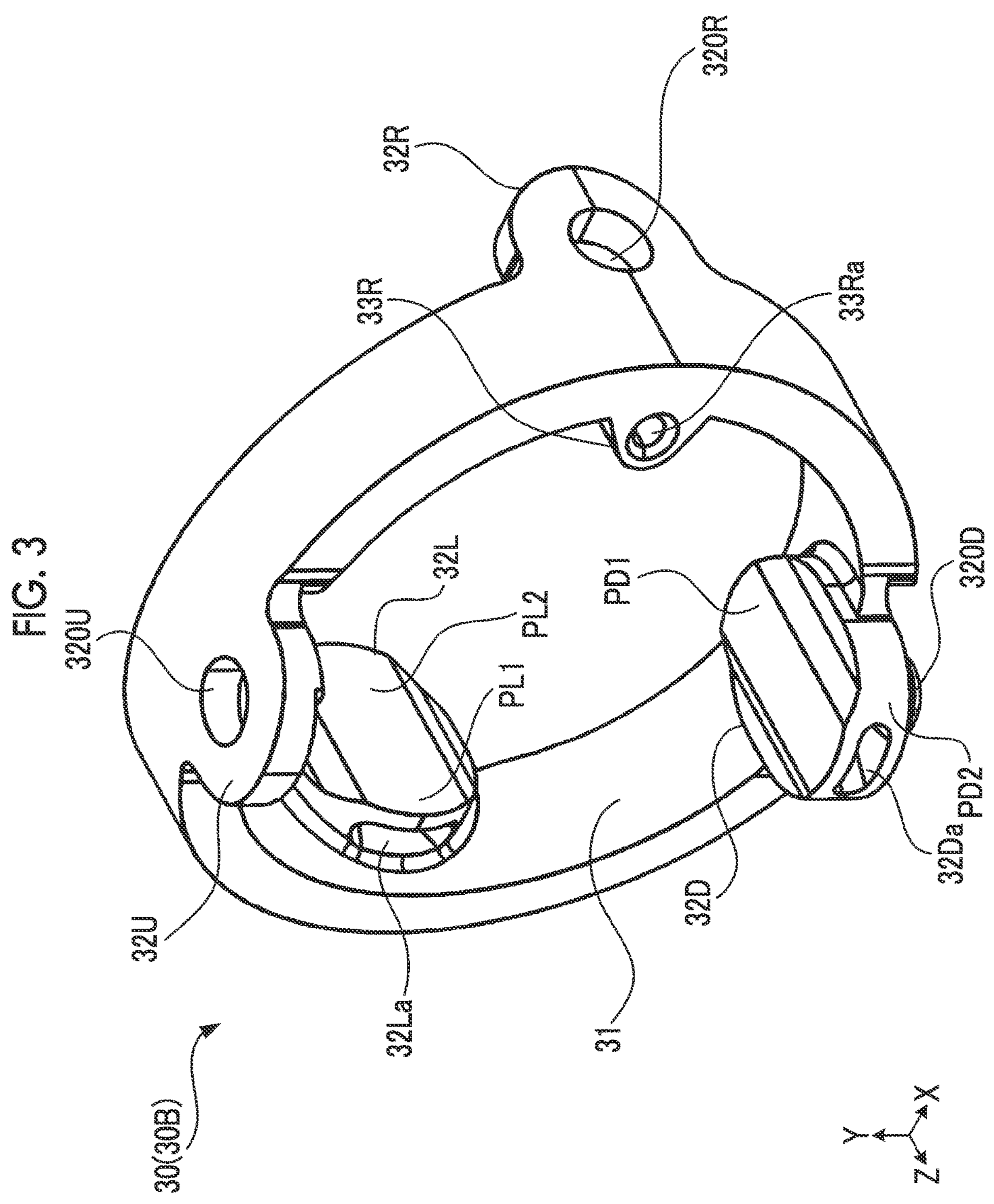
FIG. 3 is an enlarged perspective view of a movable member 30B shown in FIG. 2.
Figure 4:
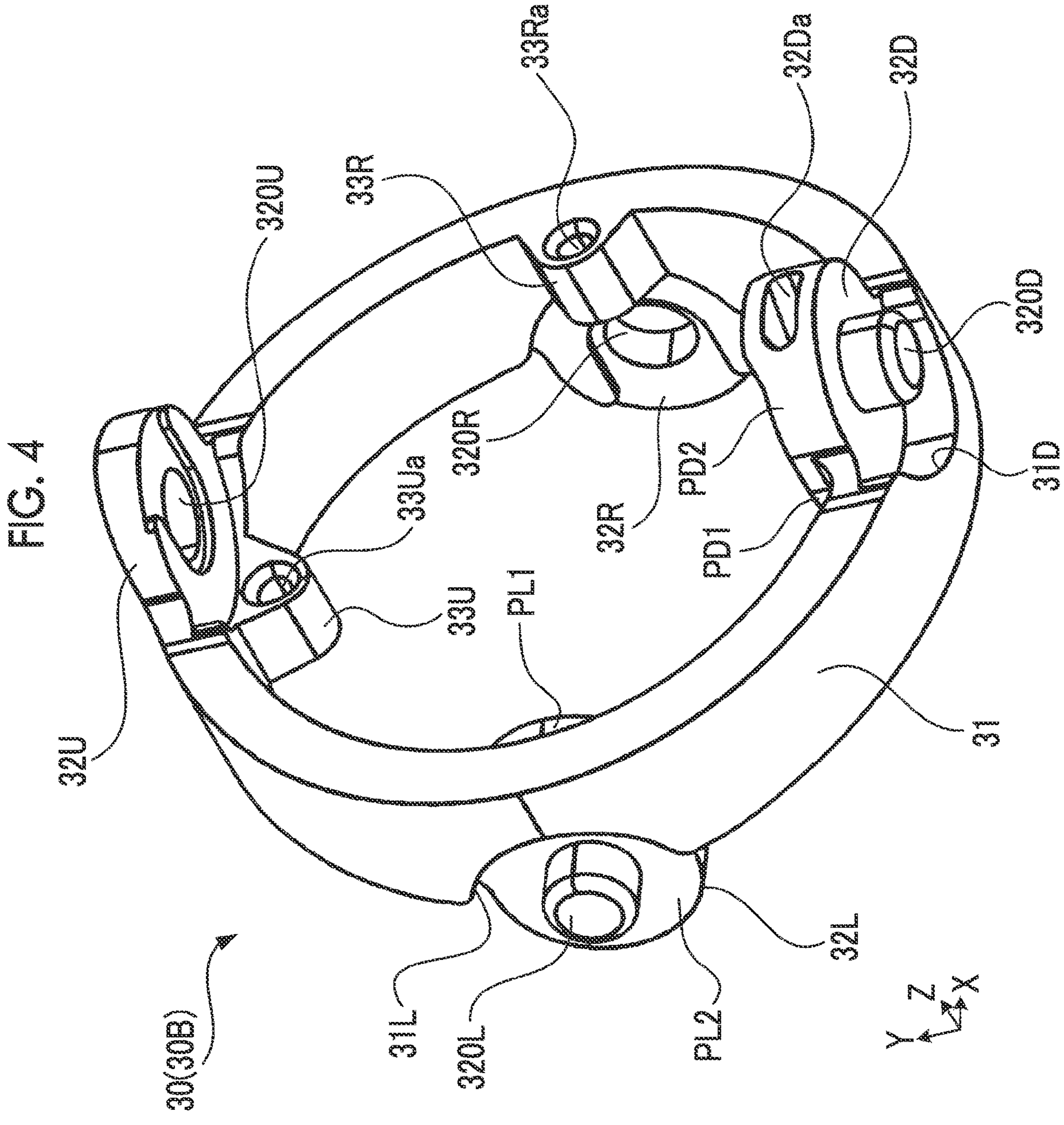
FIG. 4 is a perspective view of the movable member 30B shown in FIG. 3 as viewed from another direction.
Figure 5:
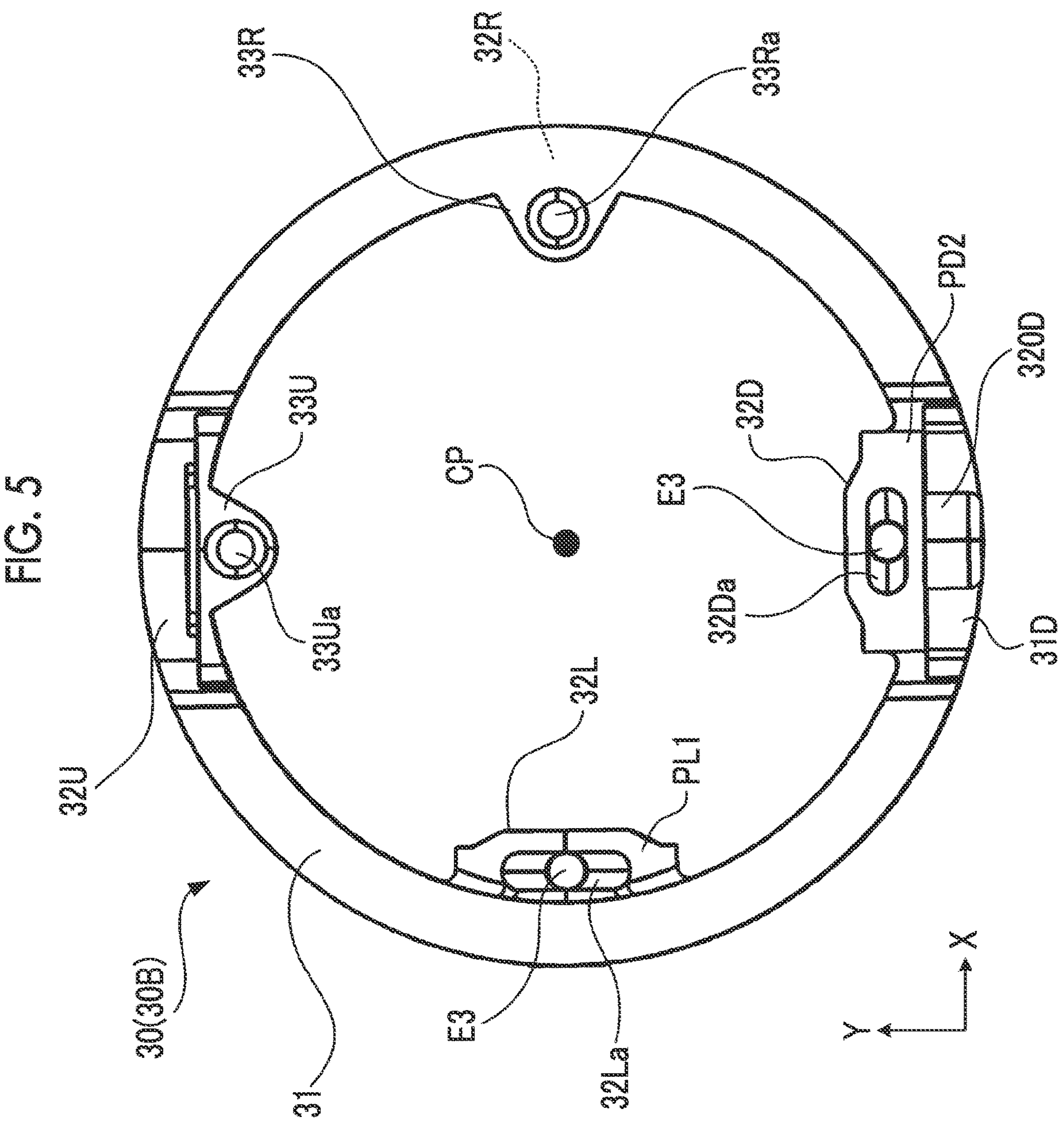
FIG. 5 is a plan view of the movable member 30B shown in FIG. 2 as viewed from a proximal end side of an insertion part 1A.

FIG. 3 is an enlarged perspective view of the movable member 30B shown in FIG. 2. FIG. 4 is a perspective view of the movable member 30B shown in FIG. 3 as viewed from another direction. FIG. 5 is a plan view of the movable member 30B shown in FIG. 2 as viewed from a proximal end side of the insertion part 1A.

The movable member 30 includes a tubular (cylindrical in the present embodiment) body part 31, a first protruding portion 32R and a first protruding portion 32L that protrude from the body part 31 to one side (a distal end side of the insertion part 1A) in the direction Z, face each other across an axis CP (see FIG. 5) of the body part 31, and are arranged in the direction X, and a second protruding portion 32U and a second protruding portion 32D that protrude from the body part 31 to the other side (a proximal end side of the insertion part 1A) in the direction Z, face each other across the axis CP, and are arranged in the direction Y. The first protruding portion 32R and the first protruding portion 32L, and the second protruding portion 32U and the second protruding portion 32D are provided at different positions (specifically, positions shifted by 90 degrees) in a circumferential direction of the body part 31.

Each of the first protruding portion 32R and the second protruding portion 32U forms a flat plate shape which protrudes in the direction Z from an end surface of the body part 31 in the direction Z and of which a thickness direction substantially coincides with a radial direction of the body part 31. The first protruding portion 32R is provided with a first hole portion 320R that extends in the radial direction (direction X) of the body part 31 and that penetrates the first protruding portion 32R. The second protruding portion 32U is provided with a second hole portion 320U that extends in the radial direction (direction Y) of the body part 31 and that penetrates the second protruding portion 32U.

The first protruding portion 32L forms a flat plate shape including a first portion PL1 that is slightly bulged in the radial direction of the body part 31 from an inner peripheral surface of the body part 31, and a second portion PL2 that protrudes in the direction Z (to the distal end side) from a distal end-side end surface of the first portion PL1 and a distal end-side end surface of the body part 31. As shown in FIG. 4, the second portion PL2 is provided with a first projecting portion 320L extending outward in the radial direction of the body part 31. At a position where the first protruding portion 32L of the body part 31 is provided, a notch 31L that receives a distal end portion of the second protruding portion 32U of the movable member 30 disposed adjacent thereto is formed.

As shown in FIGS. 3 and 5, in the first protruding portion 32L, a first through-hole 32La that penetrates the first protruding portion 32L in the direction Z is formed. The first through-hole 32La has an oval shape extending in the direction Y in plan view viewed in the direction Z, and is disposed on an inner side with respect to the inner peripheral surface of the body part 31. A wire 43 is inserted into the first through-hole 32La.

As shown in FIG. 4, the second protruding portion 32D forms a flat plate shape including a first portion PD1 that is slightly bulged in the radial direction of the body part 31 from the inner peripheral surface of the body part 31, and a second portion PD2 that protrudes in the direction Z (to the proximal end side) from a proximal end-side end surface of the first portion PD1 and a proximal end-side end surface of the body part 31. The second portion PD2 is provided with a second projecting portion 320D extending outward in the radial direction of the body part 31. At a position where the second protruding portion 32D of the body part 31 is provided, a notch 31D that receives a distal end portion of the first protruding portion 32R of the movable member 30 disposed adjacent thereto is formed.

As shown in FIGS. 4 and 5, in the second protruding portion 32D, a second through-hole 32Da that penetrates the second protruding portion 32D in the direction Z is formed. As shown in FIG. 5, the second through-hole 32Da has an oval shape extending in the direction X in plan view viewed in the direction Z, and is disposed on the inner side with respect to the inner peripheral surface of the body part 31. The wire 43 is inserted into the second through-hole 32Da.

Figure 6:
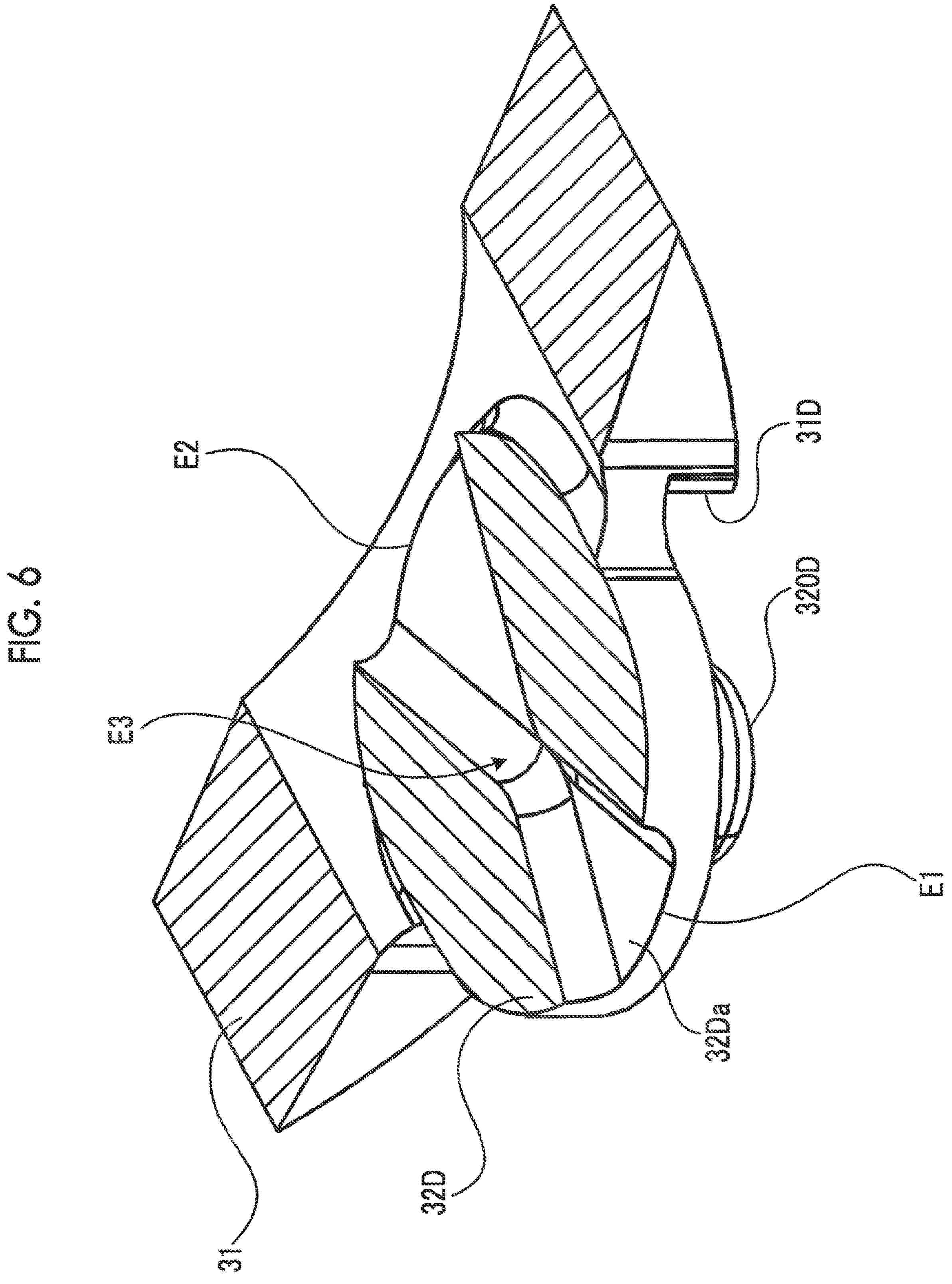
FIG. 6 is a schematic cross-sectional view of a vicinity of a second protruding portion 32D of the movable member 30B shown in FIG. 3.

FIG. 6 is a schematic cross-sectional view of a vicinity of the second protruding portion 32D of the movable member 30B shown in FIG. 3. FIG. 6 shows a cut surface perpendicular to the direction Y and passing through the second through-hole 32Da. The second through-hole 32Da of the second protruding portion 32D has a narrow portion E3, which is narrower than one end edge E1 and the other end edge E2, between the one end edge E1 and the other end edge E2.

In the second through-hole 32Da, a diameter of the narrow portion E3 is configured to be about the same as a diameter of the wire 43 inserted into the second through-hole 32Da.

Meanwhile, an opening portion is widened from the narrow portion E3 toward the one end edge E1, and the opening portion is widened from the narrow portion E3 toward the other end edge E2. A structure of the first through-hole 32La formed in the first protruding portion 32L of the movable member 30B is also the same as that of the second through-hole 32Da.

As shown in FIG. 4, the body part 31 is provided with a first insertion hole 33Ra into which the wire 43 is inserted, at the same position in the circumferential direction as the position of the first protruding portion 32R. The inner peripheral surface of the body part 31 is provided with a protruding piece 33R that protrudes radially inward, and a first insertion hole 33Ra is formed by a through-hole that penetrates the protruding piece 33R in the direction Z. The protruding piece 33R is eccentrically disposed on the proximal end side of the insertion part 1A (a side opposite to a side where the first protruding portion 32R protrudes) in the direction Z (see FIGS. 4 and 11).

In addition, the body part 31 is provided with a second insertion hole 33Ua into which the wire 43 is inserted, at the same position in the circumferential direction as the position of the second protruding portion 32U. The inner peripheral surface of the body part 31 is provided with a protruding piece 33U that protrudes radially inward, and a second insertion hole 33Ua is formed by a through-hole that penetrates the protruding piece 33U in the direction Z. The protruding piece 33U is eccentrically disposed on the distal end side of the insertion part 1A (on a side opposite to a side where the second protruding portion 32U protrudes) in the direction Z (see FIGS. 4 and 11).

As shown in FIG. 5, in a state of being viewed in the direction Z, the second insertion hole 33Ua and the narrow portion E3 of the second through-hole 32Da are disposed to face each other across the axis CP, and the narrow portion E3 of the first through-hole 32La and the first insertion hole 33Ra are disposed to face each other across the axis CP.

Figure 7:
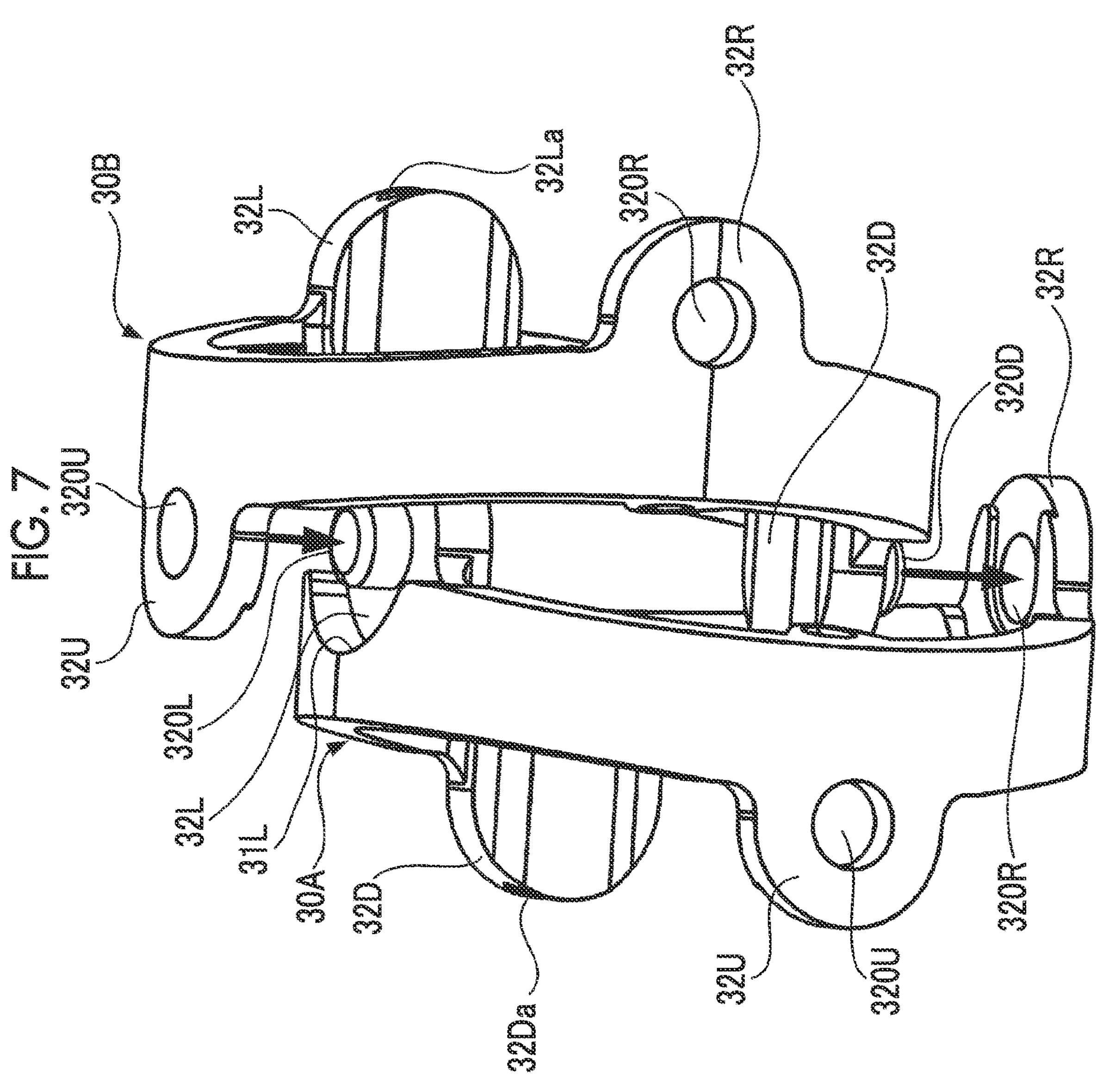
FIG. 7 is a perspective view illustrating a method of connecting a movable member 30A to the movable member 30B.
Figure 8:
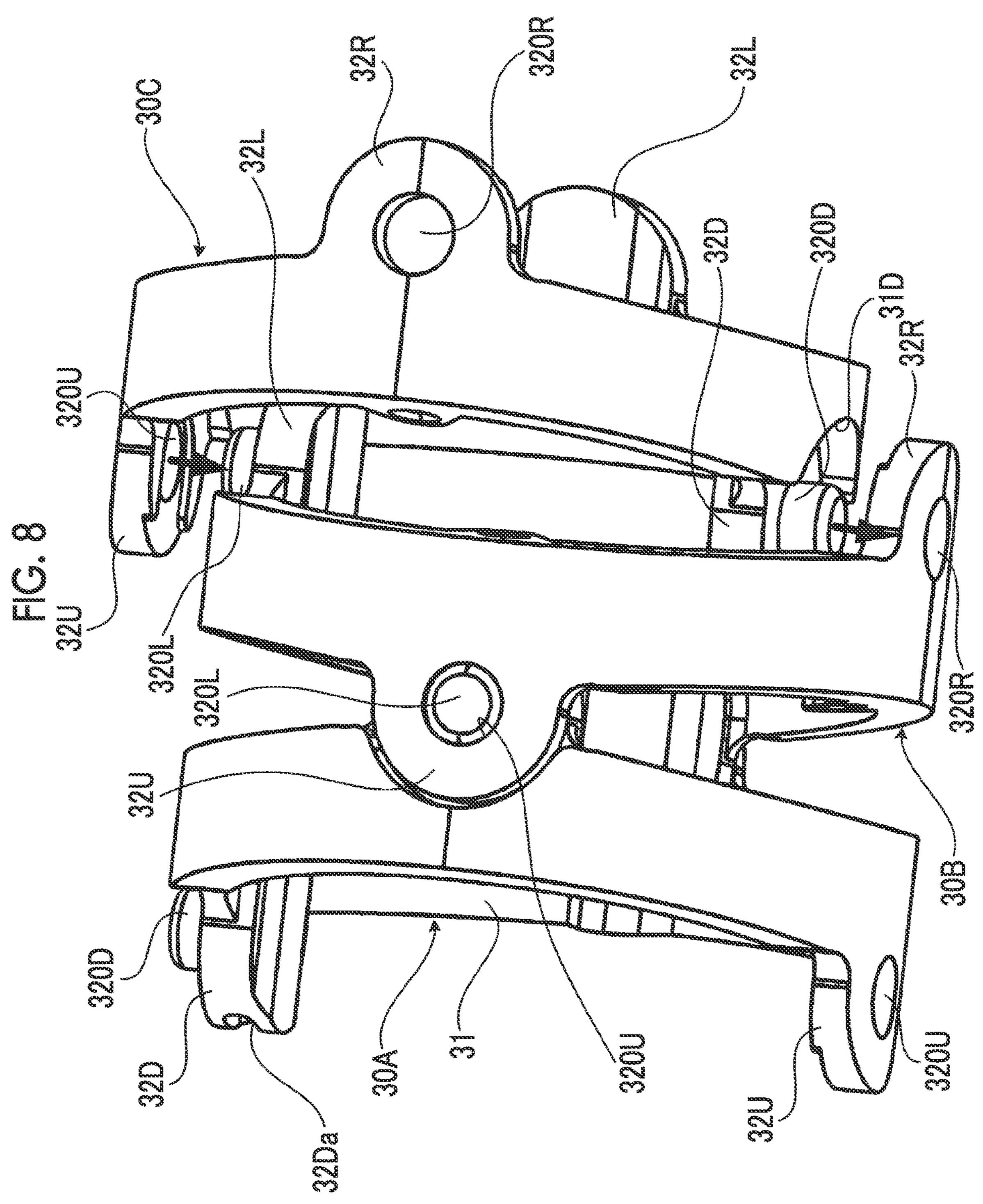
FIG. 8 is a perspective view illustrating a method of connecting a movable member 30C to a connected body of the movable member 30A and the movable member 30B.
Figure 9:
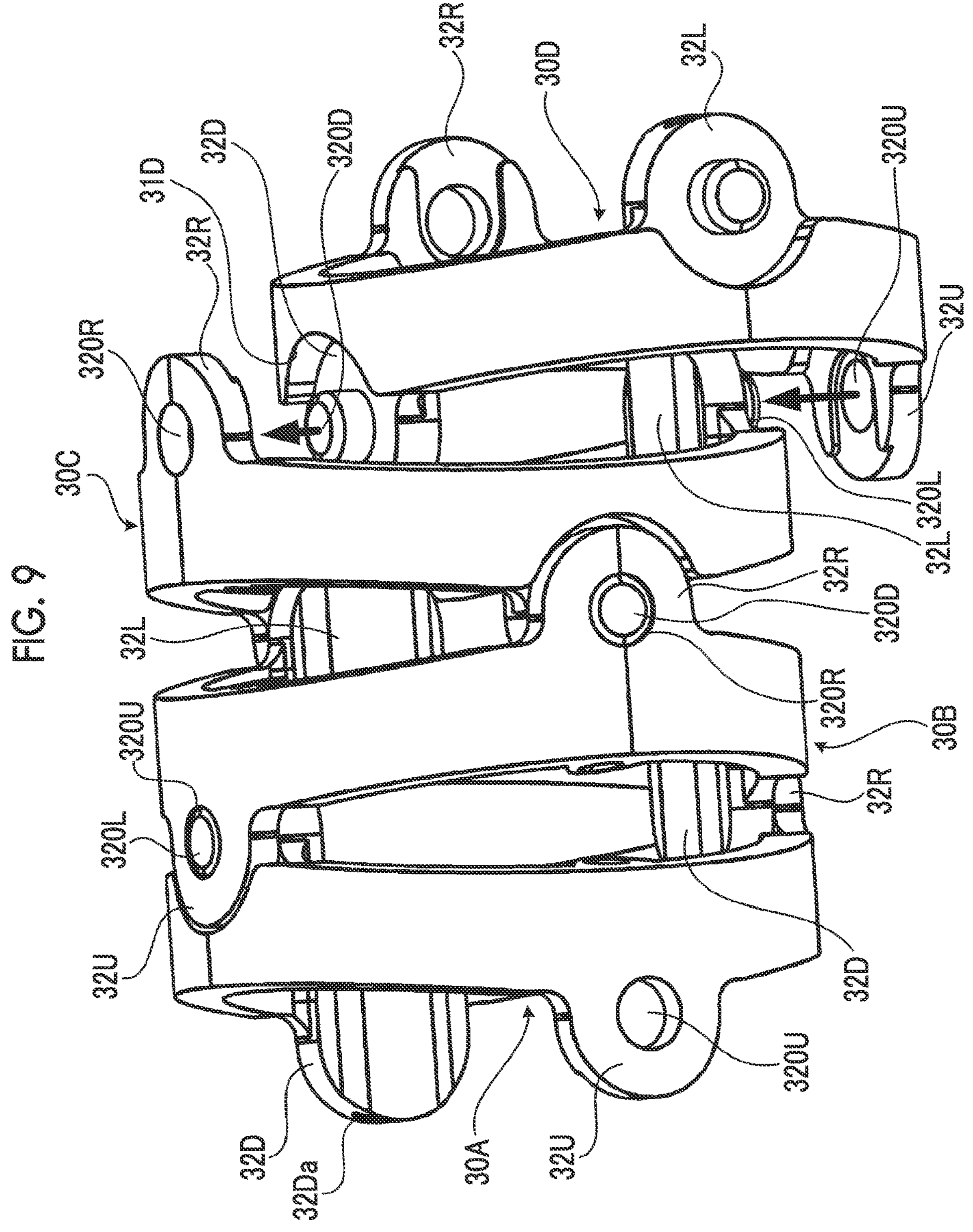
FIG. 9 is a perspective view illustrating a method of connecting a movable member 30D to a connected body of the movable member 30A, the movable member 30B, and the movable member 30C.

The movable members 30 configured as described above are connected as follows to form a movable member group 30G. FIGS. 7 to 9 are schematic views illustrating a process of forming the movable member group 30G.

First, the movable member 30A and the movable member 30B are prepared. Next, as shown in FIG. 7, the movable member 30B is rotated by 90 degrees around the axis CP with respect to the movable member 30A to obtain a state in which the second hole portion 320U of the movable member 30B is positioned above the first projecting portion 320L of the movable member 30A, and the second projecting portion 320D of the movable member 30B is positioned above the first hole portion 320R of the movable member 30A. Next, from this state, the movable member 30B is moved downward as indicated by a thick arrow in the drawing to engage the first projecting portion 320L of the movable member 30A with the second hole portion 320U of the movable member 30B and to engage the first hole portion 320R of the movable member 30A with the second projecting portion 320D of the movable member 30B. In this case, the distal end of the second protruding portion 32U of the movable member 30B is fitted into the notch 31L of the movable member 30A, and the distal end of the first protruding portion 32R of the movable member 30A is fitted into the notch 31D of the movable member 30B.

Through the above operations, the movable member 30A and the movable member 30B are connected to each other to be rotatable with the second projecting portion 320D and the first projecting portion 320L as rotation shafts.

Next, the movable member 30C is prepared, and as shown in FIG. 8, the movable member 30C is rotated by 90 degrees around the axis CP with respect to the movable member 30B. Further, a state is obtained in which the second hole portion 320U of the movable member 30C is positioned above the first projecting portion 320L of the movable member 30B, and the second projecting portion 320D of the movable member 30C is positioned above the first hole portion 320R of the movable member 30B. Next, from this state, the movable member 30C is moved downward as indicated by a thick arrow in the drawing to engage the first projecting portion 320L of the movable member 30B with the second hole portion 320U of the movable member 30C and to engage the first hole portion 320R of the movable member 30B with the second projecting portion 320D of the movable member 30C. In this case, the distal end of the second protruding portion 32U of the movable member 30C is fitted into the notch 31L of the movable member 30B, and the distal end of the first protruding portion 32R of the movable member 30B is fitted into the notch 31D of the movable member 30C.

Through the above operations, the movable member 30B and the movable member 30C are connected to each other to be rotatable with the second projecting portion 320D and the first projecting portion 320L as rotation shafts.

Next, the movable member 30D is prepared, and as shown in FIG. 9, the movable member 30D is rotated by 90 degrees around the axis CP with respect to the movable member 30C. Further, a state is obtained in which the second projecting portion 320D of the movable member 30D is positioned below the first hole portion 320R of the movable member 30C, and the second hole portion 320U of the movable member 30D is positioned below the first projecting portion 320L of the movable member 30C. Next, from this state, the movable member 30D is moved upward as indicated by a thick arrow in the drawing to engage the first projecting portion 320L of the movable member 30C with the second hole portion 320U of the movable member 30D and to engage the first hole portion 320R of the movable member 30C with the second projecting portion 320D of the movable member 30D. In this case, the distal end of the second protruding portion 32U of the movable member 30D is fitted into the notch 31L of the movable member 30C, and the distal end of the first protruding portion 32R of the movable member 30C is fitted into the notch 31D of the movable member 30D.

Through the above operations, the movable member 30C and the movable member 30D are connected to each other to be rotatable with the second projecting portion 320D and the first projecting portion 320L as rotation shafts.

Figure 10:
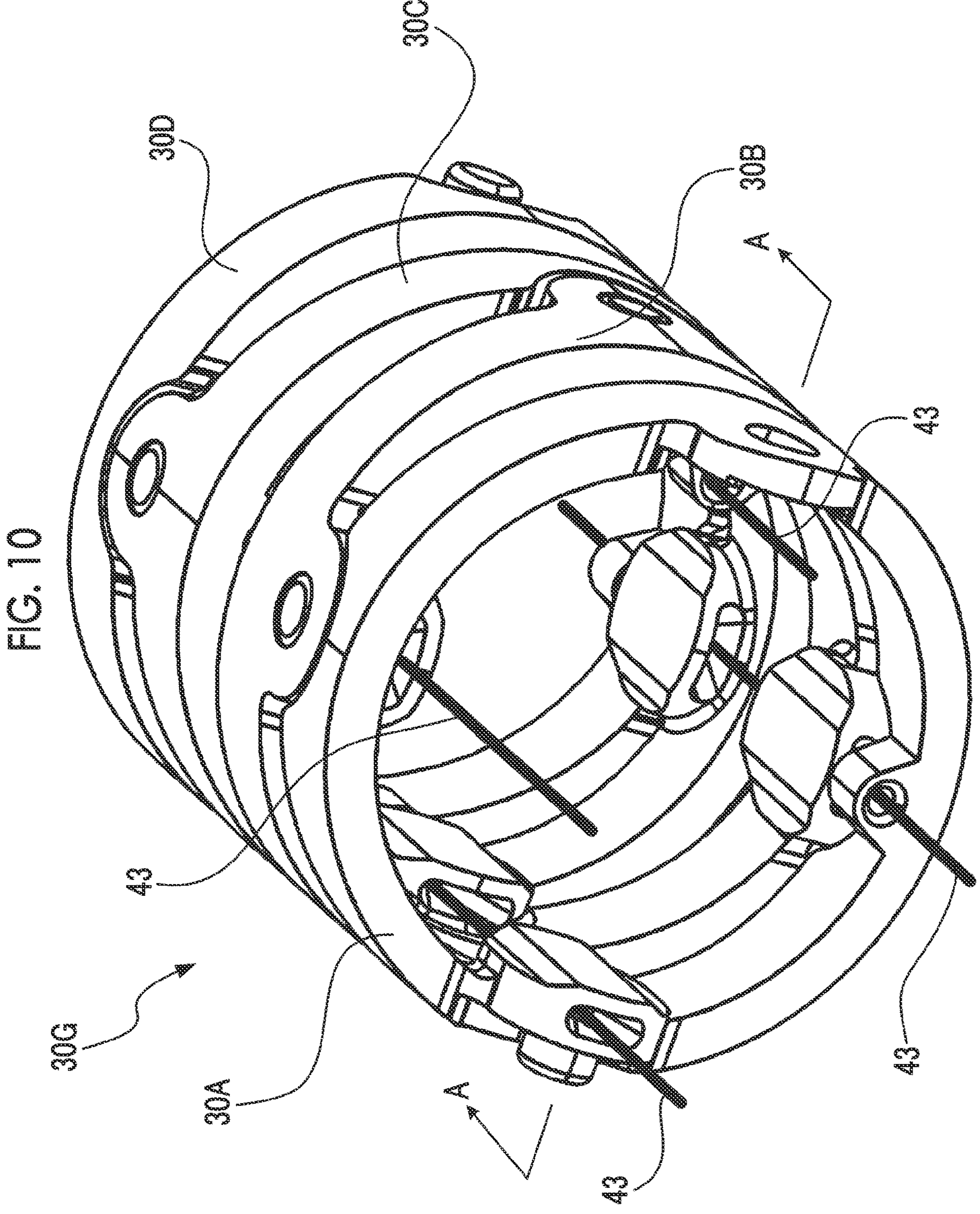
FIG. 10 is a perspective view of a movable member group 30G.

FIG. 10 is a perspective view of the movable member group 30G. After the plurality of movable members 30 are connected to each other as described above, as shown in FIG. 10, the wire 43 is inserted into the first through-hole 32La, the second through-hole 32Da, the first insertion hole 33Ra, and the second insertion hole 33Ua of each of the movable members 30.

Figure 11:
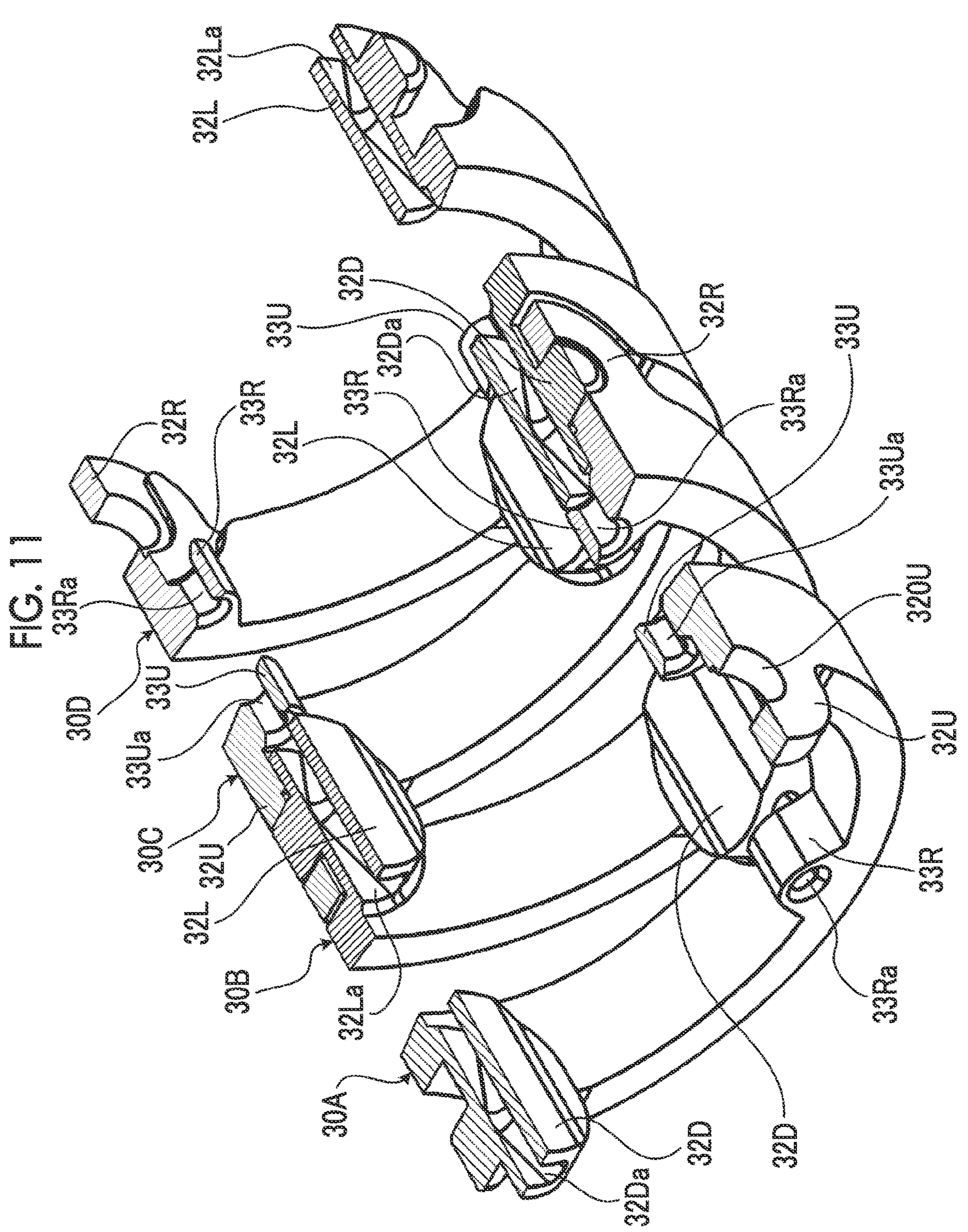
FIG. 11 is a schematic cross-sectional view taken along line A-A in FIG. 10.

FIG. 11 is a schematic cross-sectional view taken along line A-A in FIG. 10. In a state of being viewed in the direction Z, the bendable part 1*b* is in a state in which any of the first through-hole 32La, the second through-hole 32Da, the first insertion hole 33Ra, or the second insertion hole 33Ua is disposed at four positions in a circumferential direction (positions at every 90 degrees) of all the movable members 30 that are connected. Therefore, the wire 43 can be passed through all the through-holes and the insertion holes at each of the four positions. It is possible to maintain a connected state of all the movable members 30 with four wires 43.

As described above, it is possible to rotatably connect two movable members 30 by only holding the two movable members 30 in a posture relationship in which they are relatively rotated by 90 degrees and moving the two movable members 30 relatively linearly. By repeating such operations, an internal structure of the bendable part 1*b* shown in FIG. 2 can be obtained.

In the present embodiment, for example, the two movable members 30 can be connected while maintaining a constant distance between the second protruding portion 32U and the second protruding portion 32D facing the second protruding portion 32U. In other words, the two movable members 30 can be connected to each other without being deformed. The movable member 30 is a very small member, and an operation to deform the movable member 30 is not easy. Therefore, the bendable part 1*b* can be easily manufactured. In addition, since deformation of the movable member 30 is not required, durability of the movable member 30 itself can be enhanced. Further, with the bendable part 1*b*, it is possible to connect the two movable members 30 without using a connecting member such as a rivet. Therefore, it is possible to reduce a diameter and a weight of the bendable part 1*b*. In addition, since a rivet attachment step can also be removed, manufacturing can be easily performed.

In the bendable part 1*b*, as shown in FIG. 5, each of the second protruding portion 32D and the first protruding portion 32L has a portion protruding inward with respect to the inner peripheral surface of the body part 31. Accordingly, since thicknesses of the second protruding portion 32D and the first protruding portion 32L are increased, strengths of the second protruding portion 32D and the first protruding portion 32L can be increased. In addition, by forming the second through-hole 32Da and the first through-hole 32La in the portions where the thickness is increased (portions that protrude inward with respect to the inner peripheral surface of the body part 31), a space inside the movable member 30 can be effectively utilized. Further, as shown in FIG. 6, each of the second through-hole 32Da and the first through-hole 32La is not in a simple columnar shape, but in a tapered shape with a wide inlet and outlet and a narrow central portion. With such a configuration, the movement of the wire 43 in a case where the bendable part 1*b* is bent (in a case where the movable member 30 rotates) is less likely to be obstructed, so that a bending operation can be smoothly performed.

Further, in the bendable part 1*b*, as shown in FIG. 11, the protruding piece 33R is eccentrically disposed on the proximal end side of the insertion part 1A in the direction Z, and the protruding piece 33U is eccentrically disposed on the distal end side of the insertion part 1A in the direction Z. Further, for the protruding piece 33R, the second protruding portion 32D is adjacent to the distal end side of the insertion part 1A, and for the protruding piece 33U, the first protruding portion 32L is adjacent to the proximal end side of the insertion part 1A. Both the lengths of the first protruding portion 32L and the second protruding portion 32D in the direction Z are larger than the lengths of the protruding piece 33R and the protruding piece 33U in the direction Z. Therefore, for example, as shown in FIG. 11, at a connection portion between the movable member 30B and the movable member 30C, the first insertion hole 33Ra and the second through-hole 32Da adjacent thereto are disposed in most of a range from the proximal end of the movable member 30B to the distal end of the movable member 30C, and the second insertion hole 33Ua and the first through-hole 32La adjacent thereto are disposed in most of a range from the proximal end of the movable member 30B to the distal end of the movable member 30C. That is, in the connection portion between the two movable members 30, the wire 43 is accommodated in the insertion holes and the through-holes over a wide range in the direction Z (specifically, a range equal to or greater than a width of one movable member 30 in the direction Z). Therefore, the holding of the connected state between the two movable members 30 by the wire 43 can be firmly made. In addition, as described above, even in a case where the wire 43 is accommodated in the insertion holes and the through-holes over a wide range, as shown in FIG. 6, since shapes of the second through-hole 32Da and the first through-hole 32La are tapered shapes, it is possible to prevent the movement of the wire 43 from being hindered.

Figure 12:
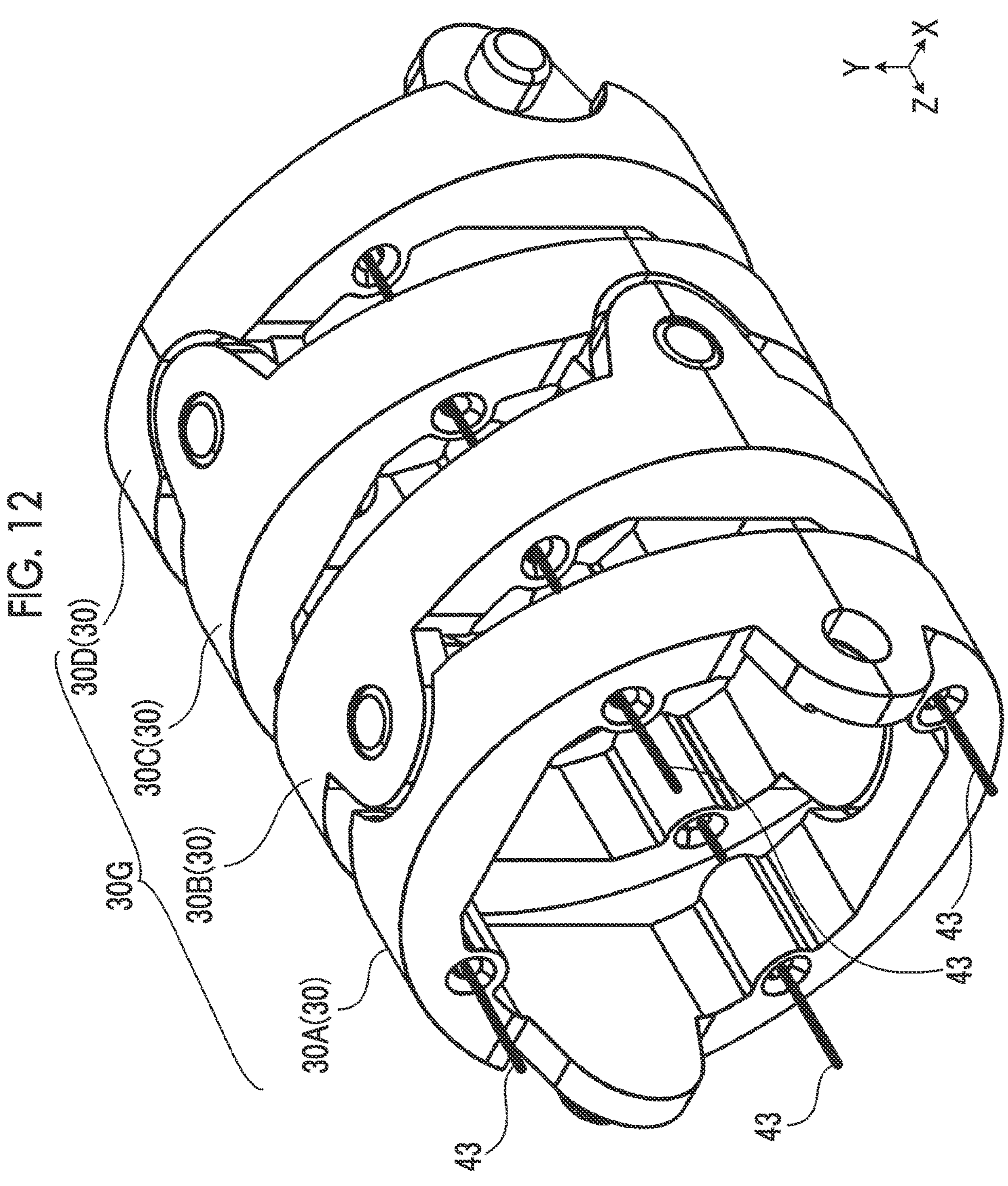
FIG. 12 is a perspective view showing a modification example of the movable member group 30G shown in FIG. 2.
Figure 13:
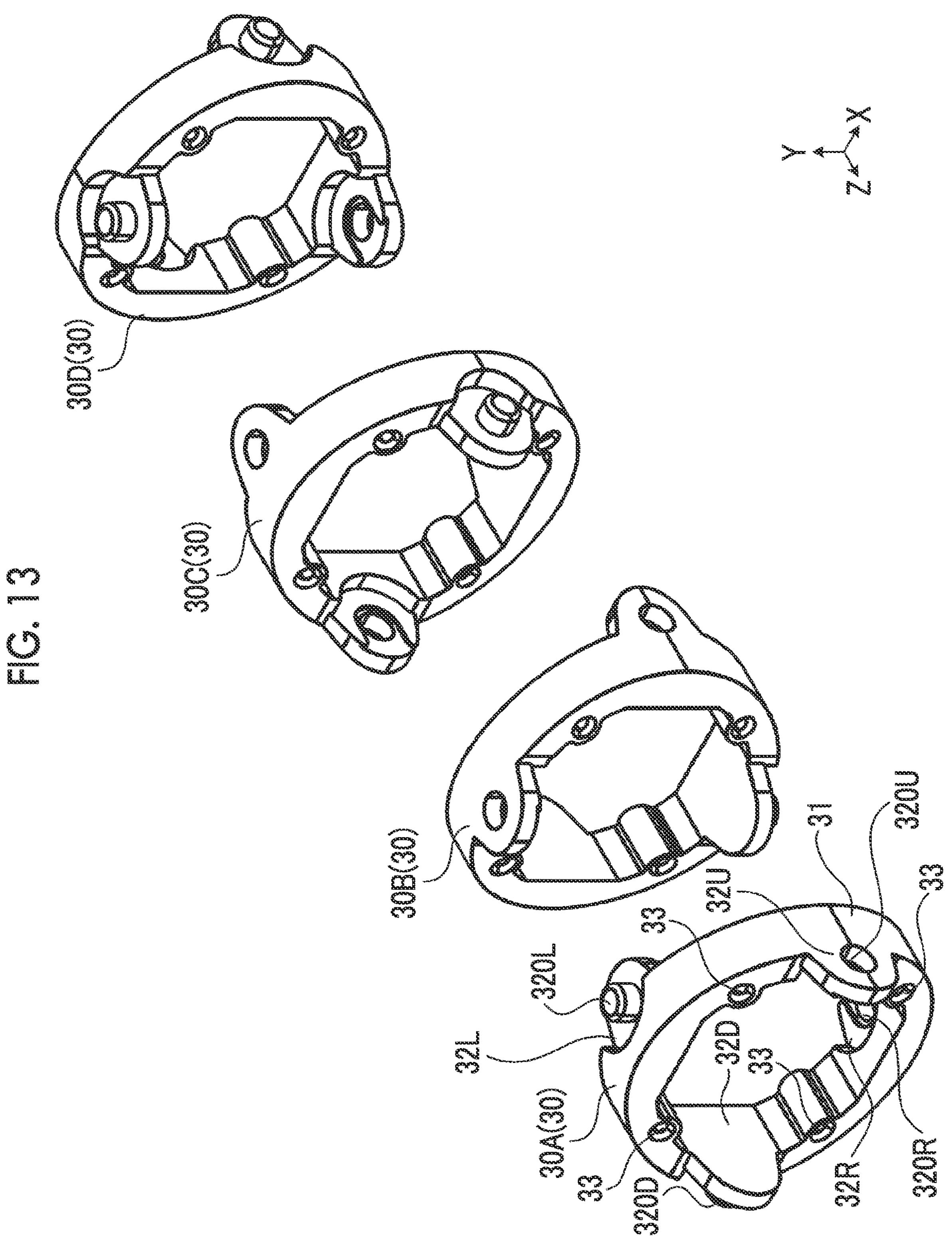

FIG. 12 is a perspective view showing a modification example of the movable member group 30G shown in FIG. 2. FIG. 13 is an exploded perspective view of the movable member group 30G shown in FIG. 12. The movable member 30 shown in this modification example has the same configuration as the movable member 30 shown in FIG. 3 except for a point that both the second protruding portion 32D and the first protruding portion 32L are made thin by removing portions protruding inward from the inner peripheral surface of the body part 31, and a point that the insertion holes 33 into which the wire 43 is inserted are provided at four positions different in the circumferential direction of the body part 31 instead of the second through-hole 32Da, the second insertion hole 33Ua, the first through-hole 32La, and the first insertion hole 33Ra.

The insertion holes 33 are formed at an intermediate position between the first protruding portion 32L and the second protruding portion 32D, an intermediate position between the first protruding portion 32L and the second protruding portion 32U, an intermediate position between the second protruding portion 32U and the first protruding portion 32R, and an intermediate position between the first protruding portion 32R and the second protruding portion 32D, and are composed of through-holes that penetrate the body part 31 in the direction Z. As described above, the insertion holes 33 are provided at positions different from the positions of the first protruding portion 32L, the first protruding portion 32R, the second protruding portion 32D, and the second protruding portion 32U in the circumferential direction.

According to this modification example, thicknesses of the second protruding portion 32D and the first protruding portion 32L can be reduced, which can contribute to making the endoscope 1 thinner.

Figure 14:
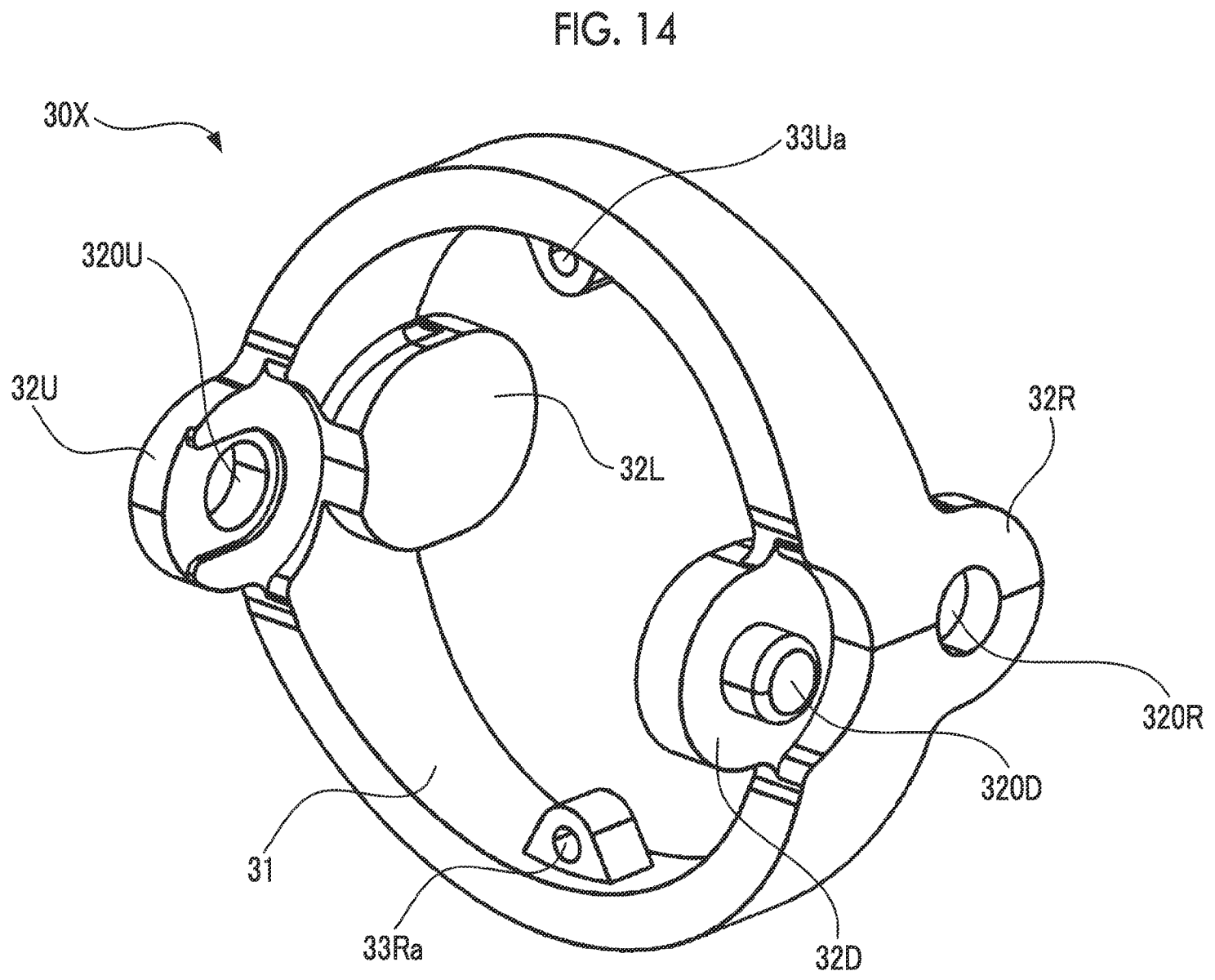

FIG. 14 is a perspective view showing a configuration of a movable member 30X which is a modification example of the movable member 30. The movable member 30X has the same configuration as the movable member 30 shown in FIG. 3 except for a point that the position of the second protruding portion 32D in the circumferential direction of the body part 31 is changed to the same position as the position of the first protruding portion 32R, a point that the second through-hole 32Da is removed, a point that the position of the second protruding portion 32U in the circumferential direction of the body part 31 is changed to the same position as the position of the first protruding portion 32L, a point that the first through-hole 32La is removed, and a point that the position of the protruding piece 33R in the circumferential direction of the body part 31 is changed to a position between the first protruding portion 32R and the first protruding portion 32L. As described above, the movable member 30X has a configuration in which the first protruding portion 32R and the first protruding portion 32L, and the second protruding portion 32U and the second protruding portion 32D are provided at the same positions in the circumferential direction of the body part 31.

Figure 15:
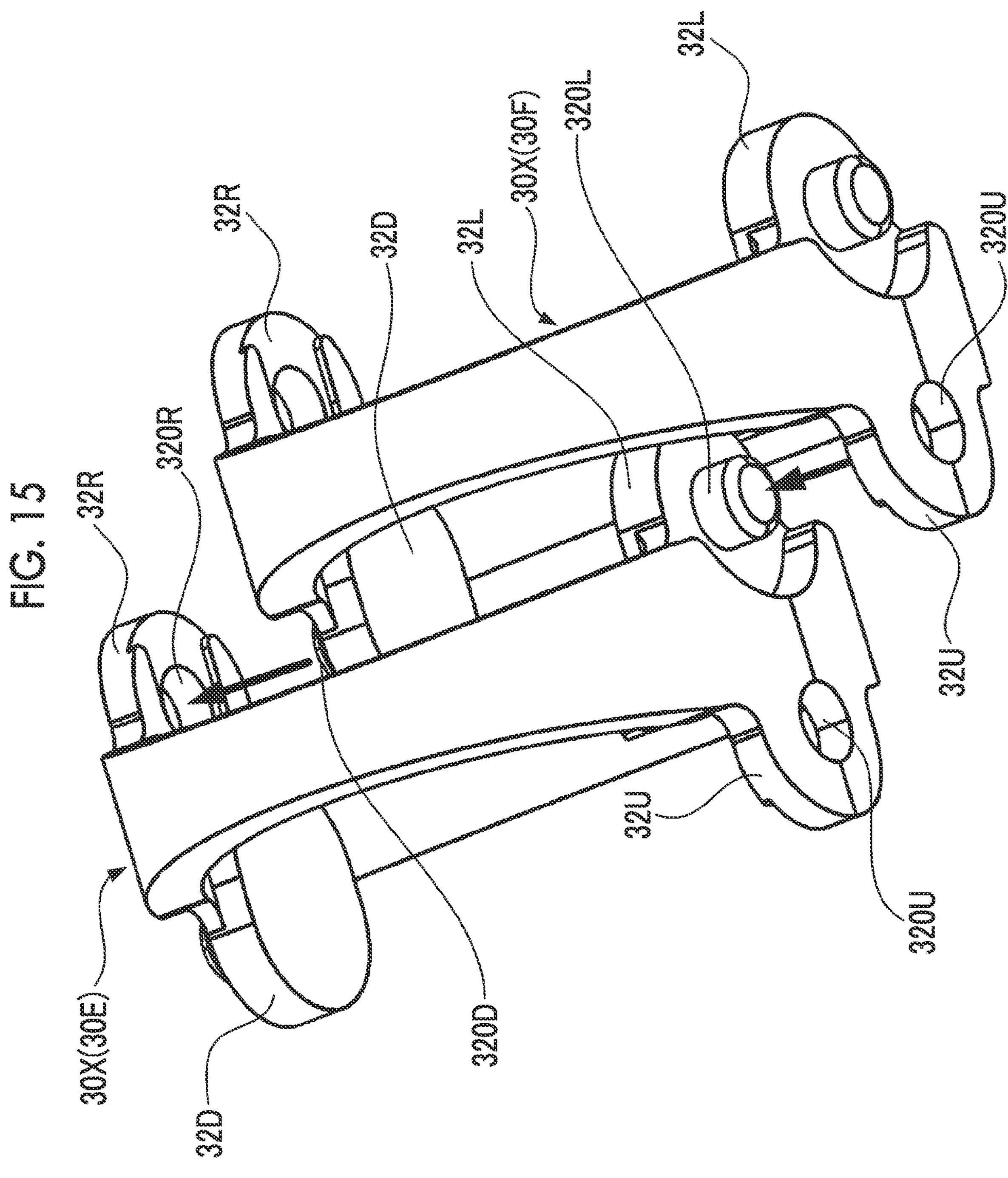
FIG. 15 is a perspective view illustrating a method of connecting two movable members 30X.
Figure 16:
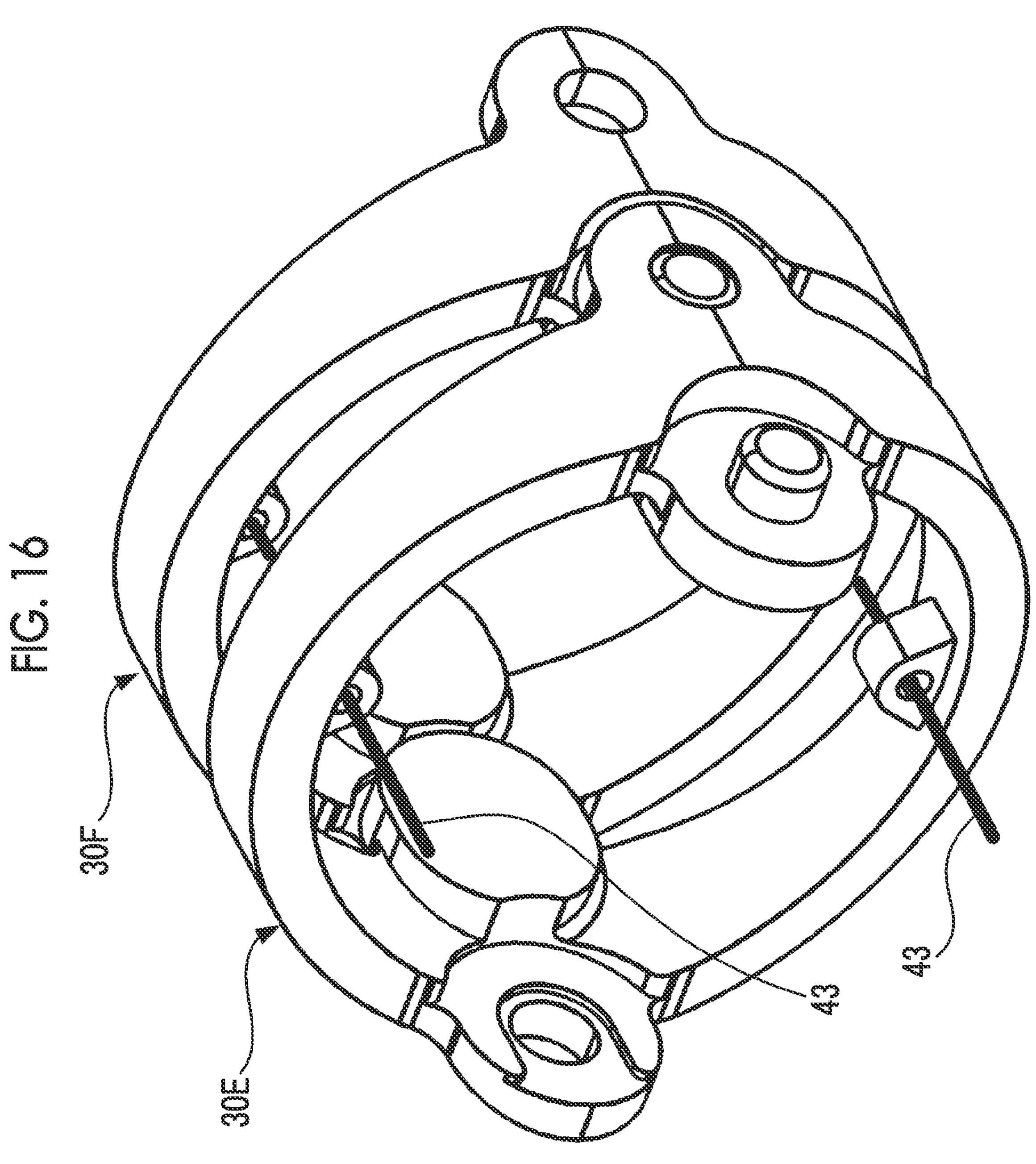
FIG. 16 is a perspective view showing a state in which the two movable members 30X are connected to each other.

In a case where two movable members 30X (described as a movable member 30E and a movable member 30F) are connected, as shown in FIG. 15, the movable member 30E and the movable member 30F are held in the same posture to obtain a state in which the first hole portion 320R of the movable member 30E is positioned above the second projecting portion 320D of the movable member 30F, and the first projecting portion 320L of the movable member 30E is positioned above the second hole portion 320U of the movable member 30F. Next, from this state, the movable member 30F is moved upward as indicated by a thick arrow in FIG. 15 to engage the first hole portion 320R of the movable member 30E with the second projecting portion 320D of the movable member 30F and to engage the first projecting portion 320L of the movable member 30E with the second hole portion 320U of the movable member 30F. Through such operations, as shown in FIG. 16, the movable member 30E and the movable member 30F are connected to each other to be rotatable with the second projecting portion 320D and the first projecting portion 320L as rotation shafts. After a plurality of the movable members 30X are connected, the wire 43 is inserted into all the first insertion holes 33Ra at the same position in the circumferential direction, and the wire 43 is inserted into all the second insertion holes 33Ua at the same position in the circumferential direction, so that a connected state of the plurality of movable members 30X is maintained.

According to the bendable part 1*b* including the movable member 30X, it is possible to rotatably connect two movable members 30X by only moving the two movable members 30X relatively linearly in the same manner as the bendable part 1*b* including the movable member 30, and manufacturing can be easily performed.

So far, an example has been described in which the second hole portion 320U and the first hole portion 320R of the second protruding portion 32U and the first protruding portion 32R are through-holes. However, each of the second hole portion 320U and the first hole portion 320R does not need to be a through-hole and may be a recessed portion having a bottom wall on an outer peripheral side of the body part 31. Further, it is possible to easily visually recognize an engaged state of the two movable members 30 by employing the through-holes, which is preferable in terms of manufacturing.

As described above, at least the following matters are described in the present specification. While corresponding constituents and the like in the embodiment described above are shown in parentheses, the present invention is not limited thereto.

(1) A bendable part of an endoscope that is a bendable part (bendable part 1*b*) provided in an insertion part (insertion part 1A) of the endoscope (endoscope 1), the bendable part comprising a plurality of movable members (movable members 30, 30X) that are arranged in an axial direction (direction Z) of the insertion part, in which the movable member includes a body part (body part 31) having a tubular shape, a pair of first protruding portions (first protruding portion 32R and first protruding portion 32L) that protrude to one side in the axial direction from the body part and that face each other across an axis (axis CP) of the body part, and a pair of second protruding portions (second protruding portion 32U and second protruding portion 32D) that protrude to the other side in the axial direction from the body part and that face each other across the axis of the body part, one (first protruding portion 32R) of the pair of first protruding portions is provided with a first recessed portion (first hole portion 320R) that extends in a radial direction of the body part, the other (first protruding portion 32L) of the pair of first protruding portions is provided with a first projecting portion (first projecting portion 320L) that extends in the radial direction, one (second protruding portion 32U) of the pair of second protruding portions is provided with a second recessed portion (second hole portion 320U) that extends in the radial direction of the body part, the other (second protruding portion 32D) of the pair of second protruding portions is provided with a second projecting portion (second projecting portion 320D) that extends in the radial direction, and in a case where one of two adjacent movable members is a first movable member and the other is a second movable member, the first recessed portion (first hole portion 320R) of the first movable member engages with the second projecting portion (second projecting portion 320D) of the second movable member, and the first projecting portion (first projecting portion 320L) of the first movable member engages with the second recessed portion (second hole portion 320U) of the second movable member.

According to (1), it is possible to connect the first movable member and the second movable member by only linearly moving the second movable member with respect to the first movable member in a state in which the first movable member and the second movable member are brought close to each other such that the first recessed portion of the first movable member and the second projecting portion of the second movable member overlap each other, and the first projecting portion of the first movable member and the second recessed portion of the second movable member overlap each other. As described above, since two movable members can be connected to each other by only moving the movable member in one direction to engage the recessed portion and the projecting portion with each other, the bendable part can be easily assembled, and the manufacturing costs can be reduced.

(2) The bendable part of an endoscope according to (1), in which in the movable member, the pair of first protruding portions and the pair of second protruding portions are provided at different positions in a circumferential direction of the body part.

According to (2), since the movable member is rotatable with each of the first projecting portion and the second projecting portion as a rotation shaft, the direction of the distal end of the insertion part can be flexibly changed, and it is possible to provide an endoscope suitable for examining a gastrointestinal tract such as a stomach and a large intestine.

(3) The bendable part of an endoscope according to (2), in which a direction in which the pair of first protruding portions are arranged is orthogonal to a direction in which the pair of second protruding portions are arranged.

According to (3), the movable member is rotatable around two rotation shafts orthogonal to each other, and the direction of the distal end of the insertion part can be flexibly changed.

(4) The bendable part of an endoscope according to (2) or (3), in which the first protruding portion (first protruding portion 32L) provided with the first projecting portion includes a first through-hole (first through-hole 32La) formed to penetrate the first protruding portion in the axial direction, the second protruding portion (second protruding portion 32D) provided with the second projecting portion includes a second through-hole (second through-hole 32Da) formed to penetrate the second protruding portion in the axial direction, and a wire (wire 43) for operating the bendable part is inserted into the first through-hole and the second through-hole.

According to (4), a plurality of the movable members can be connected to each other with the wire by using the first protruding portion provided with the first projecting portion and the second protruding portion provided with the second projecting portion. Therefore, it is possible to prevent the adjacent movable members from being disengaged from each other by the wire.

(5) The bendable part of an endoscope according to (4), in which each of the first through-hole and the second through-hole has a narrow portion (narrow portion E3) narrower than one end edge (E1) and the other end edge (E2), between the one end edge and the other end edge.

According to (5), since each of the first through-hole and the second through-hole is widened at an outlet and an inlet thereof, the movement of the wire in a case where the bendable part is bent (in a case where the movable member is moved) is less likely to be obstructed, and a bending operation can be smoothly performed. Moreover, since the narrow portion is provided, the wire can be appropriately held in the through-hole.

(6) The bendable part of an endoscope according to (4) or (5), in which the body part is provided with a first insertion hole (first insertion hole 33Ra) into which the wire is inserted at a position of the first protruding portion (first protruding portion 32R) provided with the first recessed portion (first hole portion 320R), and a second insertion hole (second insertion hole 33Ua) into which the wire is inserted at a position of the second protruding portion (second protruding portion 32U) provided with the second recessed portion (second hole portion 320U).

According to (6), the body part is provided with the insertion hole at a position corresponding to the protruding portion including the recessed portion having no room for providing the insertion hole, so that four wires can be passed through a plurality of the movable members and it is possible to operate the bendable part.

(7) The bendable part of an endoscope according to (6), in which the body part is provided with a first protruding piece (protruding piece 33R) that protrudes to an inner peripheral side and that has the first insertion hole penetrating the first protruding piece in the axial direction, at a position of the first protruding portion (first protruding portion 32R) provided with the first recessed portion (first hole portion 320R), and a second protruding piece (protruding piece 33U) that protrudes to the inner peripheral side and that has the second insertion hole penetrating the second protruding piece in the axial direction, at a position of the second protruding portion (second protruding portion 32U) provided with the second recessed portion (second hole portion 320U), and the first protruding piece and the second protruding piece are disposed to be shifted from each other in the axial direction.

According to (7), since in a state in which two movable members are connected to each other, the first protruding piece and the second protruding portion are adjacent to each other, the second protruding piece and the first protruding portion are adjacent to each other, and the through-holes and the insertion holes formed therein communicate with each other, it is possible to hold the wire in a wide range in the axial direction with a simple structure.

(8) The bendable part of an endoscope according to (7), in which the first protruding piece (protruding piece 33R) is eccentrically disposed on a side opposite to a protruding direction of the first protruding portion provided with the first recessed portion (first hole portion 320R), and the second protruding piece (protruding piece 33U) is eccentrically disposed on a side opposite to a protruding direction of the second protruding portion provided with the second recessed portion (second hole portion 320U).

According to (8), since in a state in which two movable members are connected to each other, the first protruding piece and the second protruding portion are adjacent to each other, the second protruding piece and the first protruding portion are adjacent to each other, and the through-holes and the insertion holes formed therein communicate with each other, it is possible to hold the wire in a wide range in the axial direction with a simple structure.

(9) The bendable part of an endoscope according to any one of (1) to (3), in which insertion holes (insertion holes 33) into which a wire (wire 43) for operating the bendable part is inserted are formed in the body part at positions in a circumferential direction different from positions of the pair of first protruding portions and the pair of second protruding portions.

According to (9), a plurality of the movable members can be connected to each other by a wire by using the insertion holes, and it is possible to prevent the adjacent movable members from being disengaged from each other by the wire. In addition, since it is not necessary to provide the insertion hole in the protruding portion or the like, the thickness of the protruding portion can be reduced, which can contribute to making the endoscope thinner.

(10) The bendable part of an endoscope according to (1), in which in the movable member, the pair of first protruding portions and the pair of second protruding portions are provided at the same positions in a circumferential direction of the body part.

According to (10), since the movable member is movable around one rotation shaft, it is possible to provide an endoscope that is suitable for examining a lung.

(11) An endoscope comprising the insertion part that includes the bendable part according to any one of (1) to (10).

(12) A movable member in a bendable part of an endoscope in which the bendable part is configured by connecting a plurality of the movable members arranged in an axial direction of an insertion part of the endoscope, the movable member comprising: a body part having a tubular shape; a pair of first protruding portions that protrude to one side in the axial direction from the body part and that face each other across an axis of the body part; and a pair of second protruding portions that protrude to the other side in the axial direction from the body part and that face each other across the axis of the body part, in which one of the pair of first protruding portions is provided with a first recessed portion that extends in a radial direction of the body part, the other of the pair of first protruding portions is provided with a first projecting portion that extends in the radial direction, one of the pair of second protruding portions is provided with a second recessed portion that extends in the radial direction of the body part, and the other of the pair of second protruding portions is provided with a second projecting portion that extends in the radial direction.

EXPLANATION OF REFERENCES

- 1A: insertion part
- 1*a*: soft portion
- 1*b*: bendable part
- 1*c*: distal end portion
- 1: endoscope
- PL1: first portion
- PD1: first portion
- E1: one end edge
- 2A: cable
- PL2: second portion
- PD2: second portion
- E2: other end edge
- E3: narrow portion
- 10: bending operating part
- 11: operating device
- 12: angle knob
- 30A, 30B, 30C, 30D, 30E, 30F, 30X, 30: movable member
- 30G: movable member group
- 31: body part
- 32D, 32U: second protruding portion
- 32L, 32R: first protruding portion
- 32La: first through-hole
- 32Da: second through-hole
- 33R, 33U: protruding piece
- 33Ra: first insertion hole
- 33Ua: second insertion hole
- 33: insertion hole
- 41: proximal end-side connecting member
- 42: distal end-side connecting member
- 43: wire
- 91: case
- 100: endoscope system
- 320D: second projecting portion
- 320L: first projecting portion
- 320R: first hole portion
- 320U: second hole portion

What is claimed is:

1. A bendable part of an endoscope that is provided in an insertion part of the endoscope, the bendable part comprising:

a plurality of movable members that are arranged in an axial direction of the insertion part, wherein each of the movable members includes a body part having a tubular shape, a pair of first protruding portions that protrude to one side in the axial direction from the body part and that face each other across an axis of the body part, and a pair of second protruding portions that protrude to other side in the axial direction from the body part and that face each other across the axis of the body part, one of the pair of first protruding portions is provided with a first recessed portion that extends in a radial direction of the body part, other of the pair of first protruding portions is provided with a first projecting portion that extends in the radial direction, one of the pair of second protruding portions is provided with a second recessed portion that extends in the radial direction of the body part, other of the pair of second protruding portions is provided with a second projecting portion that extends in the radial direction, wherein the first protruding portion provided with the first projecting portion includes a first through-hole formed to penetrate the first protruding portion in the axial direction, the second protruding portion provided with the second projecting portion includes a second through-hole formed to penetrate the second protruding portion in the axial direction, a wire for operating the bendable part is inserted into the first through-hole and the second through-hole, and in a case where one of two adjacent ones of the movable members is a first movable member and other of the two adjacent ones of the movable members is a second movable member, the first recessed portion of the first movable member engages with the second projecting portion of the second movable member, and the first projecting portion of the first movable member engages with the second recessed portion of the second movable member.

2. The bendable part of an endoscope according to claim 1,

Wherein, in each of the movable members, the pair of first protruding portions and the pair of second protruding portions are provided at different positions in a circumferential direction of the body part.

3. The bendable part of an endoscope according to claim 2, wherein the pair of first protruding portions are arranged at a first circumferential position about the body part, and the pair of second protruding portions are arranged at a second circumferential position about the body part that is angularly offset by approximately 90 degrees from the first circumferential position.

4. The bendable part of an endoscope according to claim 1, wherein each of the first through-hole and the second through-hole has a narrow portion narrower than one end edge and other end edge of the each of the first through-hole and the second through-hole, between the one end edge and the other end edge.

5. The bendable part of an endoscope according to claim 1, wherein the body part is provided with a first insertion hole into which the wire is inserted at a position of the first protruding portion provided with the first recessed portion, and a second insertion hole into which the wire is inserted at a position of the second protruding portion provided with the second recessed portion.

6. The bendable part of an endoscope according to claim 4, wherein the body part is provided with a first insertion hole into which the wire is inserted at a position of the first protruding portion provided with the first recessed portion, and a second insertion hole into which the wire is inserted at a position of the second protruding portion provided with the second recessed portion.

7. The bendable part of an endoscope according to claim 5, wherein the body part is provided with a first protruding piece that protrudes to an inner peripheral side and that has the first insertion hole penetrating the first protruding piece in the axial direction, at a position of the first protruding portion provided with the first recessed portion, and a second protruding piece that protrudes to the inner peripheral side and that has the second insertion hole penetrating the second protruding piece in the axial direction, at a position of the second protruding portion provided with the second recessed portion, and the first protruding piece and the second protruding piece are disposed to be shifted from each other in the axial direction.

8. The bendable part of an endoscope according to claim 6, wherein the body part is provided with a first protruding piece that protrudes to an inner peripheral side and that has the first insertion hole penetrating the first protruding piece in the axial direction, at a position of the first protruding portion provided with the first recessed portion, and a second protruding piece that protrudes to the inner peripheral side and that has the second insertion hole penetrating the second protruding piece in the axial direction, at a position of the second protruding portion provided with the second recessed portion, and the first protruding piece and the second protruding piece are disposed to be shifted from each other in the axial direction.

9. The bendable part of an endoscope according to claim 7, wherein the first protruding piece protrudes to the inner peripheral side at the position of the first protruding portion provided with the first recessed portion, and the second protruding piece protrudes to the inner peripheral side at the position of the second protruding portion provided with the second recessed portion.

10. The bendable part of an endoscope according to claim 8, wherein the first protruding piece protrudes to the inner peripheral side at the position of the first protruding portion provided with the first recessed portion, and the second protruding piece protrudes to the inner peripheral side at the position of the second protruding portion provided with the second recessed portion.

11. The bendable part of an endoscope according to claim 1, wherein insertion holes into which a wire for operating the bendable part is inserted are formed in the body part at positions in a circumferential direction different from positions of the pair of first protruding portions and the pair of second protruding portions.

12. The bendable part of an endoscope according to claim 2, wherein insertion holes into which a wire for operating the bendable part is inserted are formed in the body part at positions in a circumferential direction different from positions of the pair of first protruding portions and the pair of second protruding portions.

13. The bendable part of an endoscope according to claim 3, wherein insertion holes into which a wire for operating the bendable part is inserted are formed in the body part at positions in a circumferential direction different from positions of the pair of first protruding portions and the pair of second protruding portions.

14. The bendable part of an endoscope according to claim 1, wherein, in the movable member, the pair of first protruding portions and the pair of second protruding portions are provided at the same respective circumferential angular positions in a circumferential direction of the body part.

15. An endoscope comprising the insertion part that includes the bendable part according to claim 1.

16. A movable member in a bendable part of an endoscope in which the bendable part is configured by connecting a plurality of the movable members arranged in an axial direction of an insertion part of the endoscope, the movable member comprising:

a body part having a tubular shape;

a pair of first protruding portions that protrude to one side in the axial direction from the body part and that face each other across an axis of the body part; and a pair of second protruding portions that protrude to other side in the axial direction from the body part and that face each other across the axis of the body part, wherein one of the pair of first protruding portions is provided with a first recessed portion that extends in a radial direction of the body part, other of the pair of first protruding portions is provided with a first projecting portion that extends in the radial direction, one of the pair of second protruding portions is provided with a second recessed portion that extends in the radial direction of the body part, and other of the pair of second protruding portions is provided with a second projecting portion that extends in the radial direction, wherein the first protruding portion provided with the first projecting portion includes a first through-hole formed to penetrate the first protruding portion in the axial direction, the second protruding portion provided with the second projecting portion includes a second through-hole formed to penetrate the second protruding portion in the axial direction, and a wire for operating the bendable part is inserted into the first through-hole and the second through-hole.

* * * * *